United States Patent [19]

Clauss, Jr. et al.

[11] Patent Number: 5,223,125
[45] Date of Patent: Jun. 29, 1993

[54] OXYGEN SENSOR FOR ALUMINUM KILLED, HIGH SILICON STEEL MELTS

[75] Inventors: Harry G. Clauss, Jr., Wexford; Shawn P. Smith, Rochester, both of Pa.

[73] Assignee: General Signal Corporation, Stamford, Conn.

[21] Appl. No.: 796,528

[22] Filed: Nov. 22, 1991

[51] Int. Cl.⁵ .............................. G01N 27/26
[52] U.S. Cl. ........................ 204/423; 204/422; 204/428
[58] Field of Search .................. 204/423, 422, 428

[56] References Cited

U.S. PATENT DOCUMENTS

| | | | |
|---|---|---|---|
| 4,007,106 | 2/1977 | Hone et al. | 204/423 |
| 4,342,633 | 8/1982 | Cure . | |
| 4,717,463 | 1/1988 | Clauss . | |

OTHER PUBLICATIONS

Activity of Silica in Calcium-Aluminate Based Slags by Bahri Ozturk and R. J. Fruehan, Metallurgical Transactions B, pp. 746-749, vol. 18B, Dec. 1987.

Primary Examiner—John Niebling
Assistant Examiner—Bruce F. Bell
Attorney, Agent, or Firm—William G. Miller, Jr.; Raymond E. Smiley

[57] ABSTRACT

An improved expendable oxygen sensor particularly useful for measuring the dissolved oxygen content of an aluminum killed, high silicon steel bath is disclosed. The device has the typical closed end tube of solid electrolyte containing oxygen reference material, but differs from previous sensors in that a shield is provided which protects the solid electrolyte from being in contact with the bath until the solid electrolyte has had a chance to heat up more closely to the temperature of the steel. This shield, in one form, consists of a closed end tube positioned to surround the solid electrolyte and spaced from the solid electrolyte in order to prevent erroneous outputs from the sensor due to oxidation of the shield material.

5 Claims, 1 Drawing Sheet

OXYGEN SENSOR FOR ALUMINUM KILLED, HIGH SILICON STEEL MELTS

This invention relates to expendable immersion oxygen sensors capable of being immersed in a bath of molten metal for the determination of the oxygen dissolved in the metal and, more particularly, to an oxygen sensor for use with aluminum killed, high silicon steel melts.

BACKGROUND OF THE INVENTION

The determination of dissolved oxygen in iron and steel by immersing an electrolytic cell and temperature sensing device into the molten metal during the refining of steel has been practiced by steel companies for many years. Because of the extremely harsh conditions under which these oxygen sensors are used, the solution of many problems associated with their use must be based upon assumptions as to the cause of the problem as well as the mechanism involved in their solution.

While there has been much improvement in the reliability of the readings from the oxygen sensors of this type over the years, there continues to be the problem of initial overshoot of the output signal upon immersion, i.e., the electromotive force initially moves in a positive direction beyond the true value and then decreases slowly stabilizing at the true value. One cause of this problem, as it deals with measurements in iron or steel having low levels of oxygen in the 2 to 3 parts per million range, was solved by the structure disclosed in U.S. Pat. No. 4,717,463, issued on Jan. 5, 1988, which is hereby incorporated by reference as a part of this application. That patent discloses, among other things, the use of an open ended steel tube 36 surrounding the solid electrolyte tube 24 and extending beyond the tube 24 as a means to reduce the thermal shock to the tube 24 upon immersion of the sensor into molten metal. In the referenced patent, the tube 36 is of such an inner diameter that it does not contact the tube 24, but provides an air space between the tube 24 and tube 36. Also, as stated in the referenced patent, the tube 36 is made of corrosion resistant steel to eliminated any possibility of rusting of the tube 36, which might adversely affect measurements of oxygen at low concentration.

In aluminum killed steel melts, which typically range from 0.03% to 0.05% Al with the range of dissolved oxygen in the 2 to 5 ppm range, it has become routine in recent practice to make a measurement of dissolved aluminum by using a dissolved oxygen sensor of the type disclosed in the referenced patent. The basis for using an oxygen sensor for this measurement is set forth below:

The reaction of dissolved aluminum and oxygen is given by $$2Al + 3O = Al_2O_3,$$

The equilibrium constant is $$K = \frac{a_{Al_2O_3(s)}}{h_{Al}^2 h_O^3}.$$

where $a_{Al_2O_3}$ 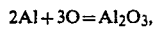

is the activity of $Al_2O_3$ with pure $Al_2O_3$ as the standard state and $h_{Al}$ and $h_O$ are the activities of Al and O for the 1 wt. % standard state. Assuming $$a_{Al_2O_3(s)} = 1,$$

then $$h_{Al}^2 = \frac{1}{Kh_O^3},$$

and at constant temperature $$\log h_{Al} = -0.5 \log K - 1.5 \log h_O.$$

For low alloy steel $h_O$ and $h_{Al}$ are equal to the weight percent of oxygen and aluminum, respectively. Because of this relationship, it can be seen that soluble aluminum (Al) is predictable as a function of dissolved oxygen (O).

In measuring the dissolved oxygen (oxygen activity) in aluminum killed (deoxidized), high silicon steel melts in which the dissolved aluminum is in the 0.03% to 0.07% range and % Si>0.1%, the output of the sensors have frequently been found to be unstable in that they produce an initial overshoot of the true oxygen level before the sensor millivolt output stabilizes. The desired response, of course, is one which rises quickly to a voltage output related to the true oxygen level with substantially no overshoot. Such a desired response is usually obtained when % Si<0.01%. A series of hypothesis were investigated to determine the cause of the undesirable overshoot. The most credible of these hypotheses is believed to be the one which postulates that there is a precipitation of silica ($SiO_2$) on a "cold" sensor. The essence of this hypothesis is set forth below.

When the sensor first enters the liquid steel it is cooler than the steel and the following reaction occurs:

$$Si + 2O \rightarrow SiO_2(s).$$

As the sensor is heated by the molten steel, the reverse reaction proceeds until equilibrium is attained. Thus $$SiO_2(s) \rightarrow Si + 2O.$$

This affects the local oxygen activity, resulting in an unstable emf output, less negative than for the true oxygen activity. Thus $$SiO_2 = Si + 2O.$$

A typical equilibrium constant for the above reaction is $$\log K = -31,000/T + 12.0,$$

where $a_{SiO_2}$ is the activity of $SiO_2$ 

and $h_{Si}$ is the activity of Si 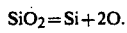

for the 1 wt. % standard state, then $$K = \frac{h_{Si} h_O^2}{a_{SiO_2}},$$

and for $h_{Si} \approx \%\ Si$ and $h_O \approx \%\ O$, $$K = \frac{[\%Si][\%O]^2}{a_{SiO_2}}.$$

Thus, if the activity of $SiO_2$ is unity, precipitation of silica will occur when the product

[% Si][% O]$^2$ exceeds $Ka_{SiO_2}$.

For an Si content of 0.3%, pure $SiO_2$, and a temperature of 1500° C. (1773° K.), this occurs when $O^2(0.3) > 10^{-31000/T+12.0}$ $O^2(0.3) > 3.28 \times 10^{-6}$ $O > 33$ ppm.

Thus, the precipitation of silica will only occur at oxygen levels greater than 33 ppm for a 0.3% Si, if the activity of silica is unity. However, the inclusions present in the steel are complex $Al_2O_3$-$MnO$-$SiO_2$ inclusions and should, therefore, have a silica activity much less than one (1). For example, if the activity of silica is 0.01, the precipitation of silica at 1500° C. and 0.3% Si can only occur above 3.3 ppm. If % $SiO_2$(in the inclusions)$\approx 20\%$, the activity of silica is 0.005 (see "Activity of Silica in Calcium-Aluminate Based Slags", by Bahri Ozturk and R. J. Fruehan, Metallurgical Transactions B, pages 746-749, volume 18B, Dec. 1987). If the temperature is increased to 1550° C., silica precipitation can only occur above 5.7 ppm. Thus, it appears that one should seek a sensor design that assures the oxygen cell is as close as possible to the molten steel temperature before molten steel contacts the cell. One critical constraint, of course, is that the total residence time of the sensor in the molten steel is limited to approximately 10 seconds because of operating conditions. Therefore, the delay of contact between the sensor and the steel bath cannot be too long or a sufficient response will not be obtained by the sensor.

The prior art related to the present invention is illustrated in FIGS. 1 and 2. FIG. 1 shows the relevant parts of the referenced U.S. Pat. No. 4,717,463. In the figures, the reference characters correspond to those in the referenced patent. Thus, the solid electrolyte tube 24 is in the form of a closed end tube of magnesium stabilized zirconia and it contains an oxygen reference material 26 above an inert filler 27 which maintains the material 26 in contact with the inner surface of tube 24. One electrical connection for the sensor is that made to the reference material 26 by conductor 28. The other electrical connection for the sensor is not shown in FIG. 1, but is shown in the referenced patent as being peripheral to the filler 34, which secures the parts of the sensor in the sensor body.

As will be noted, the prior art arrangement of FIG. 1 has an open end tube 36 which acts as a heat shield to reduce the thermal gradient along the solid electrolyte to minimize thermal breakage of that part. It is desirable to improve that arrangement to overcome the instabilities previously mention by increasing the delay between the time of immersion of the sensor and the time when molten metal contacts the solid electrolyte so that the solid electrolyte has a chance to heat up to a temperature closer to that of the bath itself than is possible with the arrangement of FIG. 1.

Another prior art arrangement is shown in FIG. 2, which illustrates the teaching of U.S. Pat. No. 4,342,633 as it would apply to the structures in U.S. Pat. No. 4,717,463. This arrangement shows the heat shield 36' as a closed end tube, suggested in the patent to be of low carbon steel, which is in contact with the solid electrolyte and serves to dampen thermal shock produced during immersion. With such an arrangement the low carbon steel of the shield would tend to cause unstable readings for the oxygen sensor because of the oxidation or rusting of the shield combined with the fact of contact between the shield and the solid electrolyte. As the shield melts, the oxygen associated with the iron oxide (rust) causes the oxygen sensor to indicate a higher oxygen activity than that which would be truly representative of the steel being tested.

It is an object of the present invention to provide an improved immersion type oxygen sensor capable of producing stable readings when the bath to be measured is an aluminum killed, high silicon melt.

According to the present invention improved sensor response is achieved with a shield protecting the solid electrolyte of the cell from contact with the steel bath until the temperature of the solid electrolyte has had a chance to more nearly approach the temperature of the bath than has been possible with the prior art with this protection being provided without contact between any oxidizing elements of the protecting shield and the solid electrolyte. Avoidance of such contact will avoid false readings due to oxidation of the shield itself.

SUMMARY OF THE INVENTION

The present invention utilizes a closed end tube of solid electrolyte having an oxygen reference material in contact with the inner surface of the tube and a first electrical conductor extending into the closed end tube to make electrical contact with the oxygen reference material. Another electrical conductor is positioned in the cartridge to provide electrical contact with the molten steel when the sensor is immersed in the bath. A shield for the solid electrolyte is provided in the form of a corrosion resistant metal tube having good thermal conductivity. The tube is closed at its end and positioned to surround the solid electrolyte but spaced from the solid electrolyte in order to allow the electrolyte to heat up before the steel bath comes in contact with the electrolyte and at the same time prevent erroneous outputs from the sensor which might occur due to oxidation of the shield material.

DESCRIPTION OF THE PREFERRED EMBODIMENTS

Figure 3:
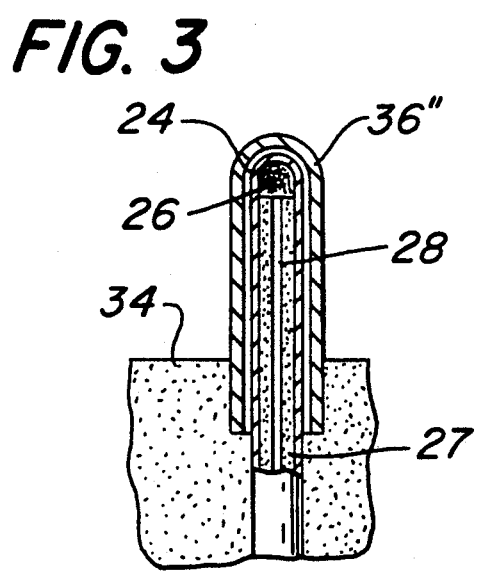
FIGS. 3, 4 and 5 are cross section diagrams illustrating different forms of the invention.
Figure 4:
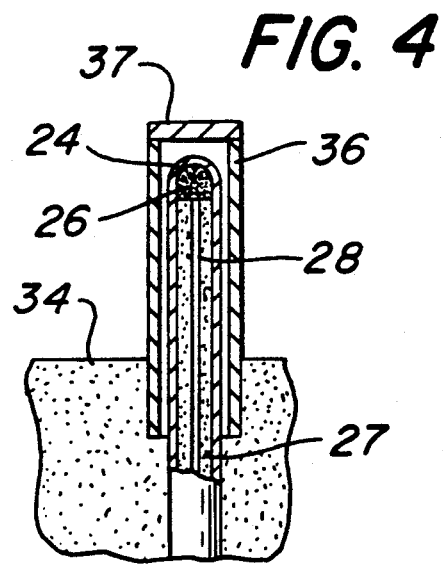
Figure 5:
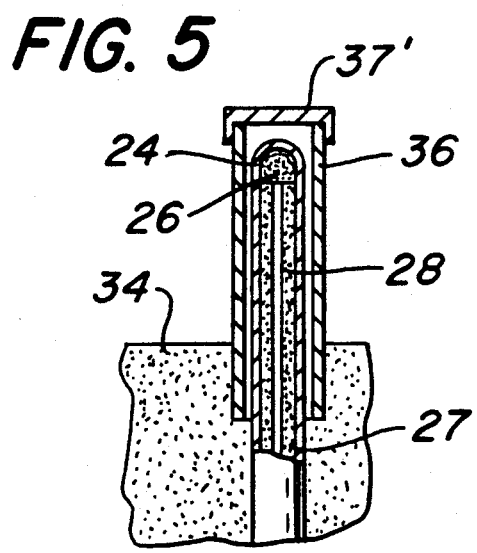

In order to provide the desired stable readings for a dissolved oxygen measurement in aluminum killed, high silicon steel melts in which the aluminum is in the 0.03% to 0.07% range and the silicon content is above 0.1%, it is necessary to heat up the solid electrolyte to a temperature as close to that of the molten steel as is possible before the solid electrolyte is exposed to the molten steel. To this end the solid electrolyte is shielded from the molten steel bath for at least 5 seconds, as by a closed corrosion resistant tube 36, as shown in FIGS. 3, 4, and 5. The tube 36 may be a stainless steel tube, for example, to provide good thermal conductivity to allow a maximum heating of the electrolyte in the 5 second period available.

Figure 1:
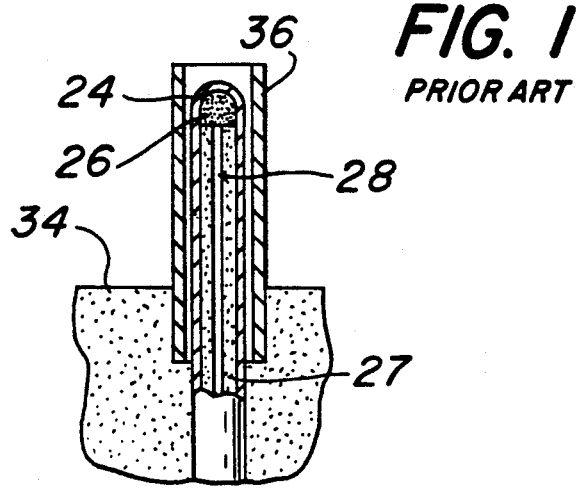
FIG. 1 is a cross section diagram illustrating the relevant parts of the referenced prior art U.S. Pat. No. 4,717,436.
Figure 2:
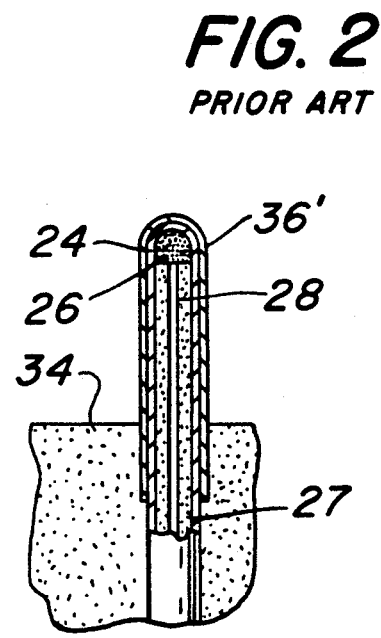
FIG. 2 is a cross section diagram illustrating the teaching of prior art U.S. Pat. No. 4,342,633.

In FIG. 3 a closed end tube 36" similar to the closed end tube 36' of the prior art (FIG. 2) may be used as ling as the shield is spaced a small distance from the solid electrolyte, as shown in FIG. 3, in order to prevent any corrosion on the shield from contacting the solid electrolyte. Alternatively, the structure of FIG. 1 may be altered by having its end closed by a combustible cover 37 cemented over the end of tube 36, as shown in FIG. 4. This cover may be a 0.030 in. thick paper disc, for example. As another alternative, the end of the tube 36 may be closed by a metal or alloy cap 37' in place of the paper disc, as shown in FIG. 5.

It has been found that the tubes 36 and 36" may advantageously be made of stainless steel having a thickness of 0.010 inches, so that upon immersion of the sensor into molten steel, the shield will not melt or dissolve in less than the initial 5 second period mentioned above.

While the present invention has particular utility in measuring dissolved oxygen in aluminum killed, high silicon steel melts, it is also useful in making oxygen measurements in other types of melts, for it improves the operation of the device of referenced U.S. Pat. No. 4,717,463 in any type of melt. In particular, the improvement provided by closing the end of tube 36 helps not only to prevent thermal shock to the tube 24 it also helps to prevent the possibility of slag contacting the solid electrolyte 24 if there is failure of other elements of the sensor cartridge designed to protect the device as it is immersed through the slag layer of the melt being measured.

What is claimed is:

1. An oxygen sensor of the expendable immersion type for measuring the dissolved oxygen content of a molten steel bath comprising:
   a sensor cartridge having a body portion;
   a slag protecting cap covering one face of said body portion;
   a closed end tube of solid electrolyte mounted in said body with said closed end of said tube extending from said one face of said body under said slag protecting cap;
   an oxygen reference material mounted within said closed end tube and in contact with the inner surface of said tube;
   a first electrical conductor extending through said cartridge and into said closed end tube making electrical contact with said oxygen reference material;
   a second electrical conductor positioned in said cartridge to provide electrical contact with said molten steel when said sensor is immersed in said bath; and
   a shield in the form of a closed end tube having good thermal conductivity and positioned under said slag protecting cap so as to surround said tube of solid electrolyte with a small space between said shield and said solid electrolyte to allow heating of the solid electrolyte before melting of said shield occurs and to, at the same time, prevent erroneous outputs from said sensor due to oxidation of the shield material.

2. A sensor as set forth in claim 1 in which said shield is single piece, closed end corrosion resistant metal tube.

3. A sensor as set forth in claim 1 in which said shield includes an open ended corrosion resistant metal tube having a combustible cover closing said open end of said shield.

4. A sensor as set forth in claim 1 in which said shield includes an open ended corrosion resistant metal tube having a metal cup covering said open end.

5. In an oxygen sensor of the expendable immersion type for measuring the dissolved oxygen content of a molten steel bath where said sensor is of the type which has body portion with a slag protecting cap covering one face thereof, a closed end tube of solid electrolyte projecting from said one face under said slag protecting cap with an oxygen reference material mounted within said tube and in contact with the inner surface of the tube and having a first electrical conductor extending into said tube so as to make electrical contact with the oxygen reference material with a second electrical conductor positioned to provide electrical contact with the molten steel when said sensor is immersed in the bath, the improvement comprising
   a shield under said slag protecting cap for protecting said solid electrolyte from contact with said steel bath for an initial period of an immersion of the sensor into the bath, said shield having a closed end and being constructed of corrosion resistant material of good thermal conductivity so that it causes the solid electrolyte to heat up before said steel bath comes in contact with said electrolyte, said shield being spaced from said electrolyte by a small distance so that there is no oxidizable material in contact with said solid electrolyte during immersion of the sensor.

* * * * *